(12) United States Patent
Palumbo et al.

(10) Patent No.: US 7,767,717 B2
(45) Date of Patent: Aug. 3, 2010

(54) TREATMENT AND PREVENTION OF EXCESSIVE SCARRING WITH 4-HYDROXY TAMOXIFEN

(75) Inventors: Andrew Palumbo, Brooklyn, NY (US); Julius Few, Chicago, IL (US); Dana Hilt, Ellicott City, MD (US)

(73) Assignees: Ascend Therapeutics, Inc., Herndon, VA (US); Northwestern University, Evanston, IL (US)

( * ) Notice: Subject to any disclaimer, the term of this patent is extended or adjusted under 35 U.S.C. 154(b) by 1235 days.

(21) Appl. No.: 10/858,399

(22) Filed: Jun. 2, 2004

(65) Prior Publication Data

US 2005/0032910 A1 Feb. 10, 2005

Related U.S. Application Data

(60) Provisional application No. 60/476,618, filed on Jun. 9, 2003.

(51) Int. Cl.
*A01N 37/22* (2006.01)
*A61K 8/02* (2006.01)
(52) U.S. Cl. .................................. 514/651; 424/401
(58) Field of Classification Search ................ 514/651; 424/401
See application file for complete search history.

(56) References Cited

U.S. PATENT DOCUMENTS

| | | | |
|---|---|---|---|
| 4,919,937 A | 4/1990 | Mauvais-Jarvis et al. |
| 4,973,755 A | 11/1990 | Grafe et al. |
| 5,045,553 A | 9/1991 | Ueda et al. |
| 5,552,162 A | 9/1996 | Lee |
| 5,613,958 A | 3/1997 | Kochinke et al. |
| 5,720,963 A | 2/1998 | Smith |
| 6,013,270 A | 1/2000 | Hargraves et al. |
| 6,503,894 B1 | 1/2003 | Dudley et al. |
| 2003/0087885 A1 | 5/2003 | Masini-Eteve et al. |
| 2004/0086552 A1 | 5/2004 | Klokkers et al. |
| 2004/0138314 A1 | 7/2004 | Bua |
| 2005/0031695 A1 | 2/2005 | Rouanet et al. |
| 2005/0032909 A1 | 2/2005 | Lignieres et al. |
| 2005/0158388 A1 | 7/2005 | Le Nestour et al. |
| 2005/0208139 A1 | 9/2005 | Hilt et al. |
| 2005/0209340 A1 | 9/2005 | Le Nestour |
| 2006/0105041 A1 | 5/2006 | Masini-Eteve |

FOREIGN PATENT DOCUMENTS

| | | |
|---|---|---|
| DE | 38 36 862 A1 | 5/1990 |
| EP | 513 832 | 11/1992 |
| EP | 1 579 856 A1 | 9/2005 |
| EP | 1 579 857 A1 | 9/2005 |
| WO | WO 94/02130 A | 2/1994 |

OTHER PUBLICATIONS

Malet et al.,"Effect of 4-hydroxytamoxifen isomers on growth and ultrastructural aspects of normal human breast epithelial (HBE) cells in culture," 2002, Journal of Steroid Biochemistry and Molecular Biology, vol. 82, pp. 289-296.*
Mutschler et al., "2.1 Drug Administration," 1991, Drug Actions, 6th edition, pp. 6-9.*
Ian S. Fentiman, "Tamoxifen and Mastalgia An Emerging Indication", Drugs 32 477-480 (1986), pp. 477-480.
Ashini L. Wijayaratne et al., "Comparative Analyses of Mechanistic Differences Among Antiestrogens", Endocrinology, vol. 140, No. 2, pp. 5828-5840.
Eric C. Dietze et al., "Tamoxifen but Not 4-Hydroxytamoxifen Initiates Apoptosis in p53(-) Normal Human Mammary Epithelial Cells by Inducing Mitochondrial Depolarization", The Journal of Biological Chemistry vol. 276, No. 7, Issue of Feb. 16, 2001, pp. 5384-5394.
Dorothy Chau et al., Tamoxifen Downregulates TGF-β Production in Keloid Fibroblasts, Annals of Plastic Surgery, vol. 40, No. 5, May 1998, pp. 490-493.
Anthony A. Mikulec et al., "Effect of Tamoxifen on Transforming Growth Factor β1 Production by Keloid and Fetal Fibroblasts", Arch Facial Plast Surg/vol. 3, Apr.-Jun. 2001 pp. 111-114.
Bronaugh & Maibach, "Percutaneous Absorption Drugs-Cosmetics-Mechanisms-Methodology", Marcel Dekker Inc., New York, 1999.
Philip Carthew et al., "Cumulative exposure to tamoxifen: DNA adducts and liver cancer in the rat", Arch Toxicol (2001) 75: 375-380.
Lawrence H. Block Ph.D., Epidermal and Transdermal Drug Delivery, Medicated Topicals, Chapter 44, pp. 836-857.
David W. Robertson et al., "Tamoxifen Antiestrogens, a Comparison of the Activity, Pharmacokinetics, and Metabolic Activation of the *CIS* and *Trans* Isomers of Tamoxifen" Journal of Steroid Biochemistry, vol. 16, pp. 1-13, (1982).
Fabrice Sauvez et al., "Cutaneously applied 4-hydroxytamoxifen is not carcinogenic in female rats", Carcinogenesis vol. 20, No. 5, pp. 843-850 1999.
Margaret Ah et al., The inhibitory effect of Tamoxifen on Human Dermal Fibroblast-Populated Collagen Lattices, Chin. J. Plast. Surg. May 2002, vol. 18, No. 3, pp. 160-162.
David W. Robertson et al., "Synthesis of the *E* and *Z* Isomers of the Antiestrogen Tamoxifen and Its Metabolite, Hydroxytamoxifen, in Tritium-Labeled Form", J. Org. Chem., 1982, vol. 47, No. 12, pp. 2387-2393.
Henri Pujol et al., "Phase I Study of percutaneous 4-hyroxy-tamoxifen with analyses of 4-hydroxytamoxifen concentrations in breast cancer and normal breast tissue", Cancer Chemother. Pharmacol. (1995) 36:493-498.
Pierre Mauvais-Jarvis et al., "trans-4-Hydroxytamoxifen Concentration and Metabolism after Local Percutaneous Adminstration to Human Breast", Cancer Research, vol. 46, Mar. 1986, pp. 1521-1525.
Catherine Malet et al., "Tamoxifen and Hydroxytamoxifen Isomers *versus* Estradiol Effects on Normal Human Breast Cells in Culture", Cancer Research, vol. 48, No. 24, Dec. 15, 1988, pp. 7193-7199.

(Continued)

*Primary Examiner*—Gina C Yu
(74) *Attorney, Agent, or Firm*—Foley & Lardner LLP

(57) ABSTRACT

The present invention provides a method for treating or preventing excessive scarring, including keloid and hypertrophic scars, by administering 4-hydroxy tamoxifen to a patient with excessive scarring or a wound at risk for developing excessive scarring.

19 Claims, 2 Drawing Sheets

OTHER PUBLICATIONS

George G.J.M. Kuiper et al., "Comparison of the Ligand Binding Specificity and Transcript Tissue Distribution of Estrogen Receptors α and β", Endocrinology, vol. 138, No. 3, 1997, pp. 863-870.

V. Craig Jordan et al., "Metabolites of tamoxifen in animals and man: identification, pharmacology, and significance", Breast Cancer Research and Treatment, 2, pp. 123-138.

"First results from the International Breast Cancer Intervention Study (IBIS-I): a randomized prevention trial", The Lancet, vol. 360, Sep. 14, 2002, pp. 817-824.

N. Giambiagi et al., "Immunological Differences Between the Estradiol-, Tamxifen- and 4-Hydroxy-Tamoxifen-Estrogen Receptor Complexes Detected by Two Monoclonal Antibodies", J. Steroid Biochem. vol. 30, No. 1-6, pp. 213-217, 1988.

I.S. Fentiman et al., "Studies of tamoxifen in women with mastalgia", The British Journal of Clinical Practice, Supplement 68, vol. 43, No. 11, Nov. 1989, pp. 34-36.

I.S. Fentiman et al., "Dosage and duration of tamoxifen treatment for mastalgia: a controlled trial", BR. J. Surg. Sep. 1988, vol. 75, No. 9, pp. 845-846.

Kuttenn et al., "Médecine Et Thérapeutique" C.R. Acad. Sc. Paris, t. 300 Serie III, No. 12, pp. 457-463 (1985).

Ian S. Fentiman, "Tamoxifen and Mastalgia An Emerging Indication", Drugs 32 477-480 (1986), pp. 477-480.

Eric C. Dietze et al., "Tamoxifen but Not 4-Hydroxytamoxifen Initiates Apoptosis in p53(-) Normal Human Mammary Epithelial Cells by Inducing Mitochondrial Depolarization", The Journal of Biological Chemistry vol. 276, No. 7, Issue of Feb. 16, 2001, pp. 5384-5394.

Gerard Chetrite et al., "Effect of Promegestone, Tamoxifen, 4-Hydroxytamoxifen and ICI 164,384 on the Oestrone Sulphatase Activity of Human Breast Cancer Cells", Anticancer Research 13: 931-934 (1993).

D. Hu et al., "Topical Tamoxifen—a potential therapeutic regime in treating excessive dermal scarring?", British Journal of Plastic Surgery (1998), 51, pp. 462-469.

Pujol, H., et al., "Phase I Study of percutaneous 4-hydroxy-tamoxifen with analyses of 4-hydroxytamoxifen concentrations in breast cancer and normal breast tissue", Cancer Chemother Pharmacol, vol. 36, pp. 493-498 (1995).

Alberti, Ingo; "In vivo assessment of enhanced topical delivery of terbinafine to human stratum corneum"; Journal of Controlled Release 71 (2001) pp. 319-327.

Dahai Hu et al., "The Inhibitory effect of tamoxifen on human dermal fibroblast-populated collagen lattices", Chin. J. Plast. Surg., May 2002, vol. 18, No. 3, pp. 160-162.

Lawrence H. Block PhD "Epidermal and Transdermal Drug Delivery", the Science and Practice of Pharmacy, Medicated Topicals, pp. 836-857 (2000).

Ruland et al.; "Influence of Various Penetration Enhancers on the in Vitro Permeation of Amino Acids Across Hairless Mouse Skin"; 1992, International Journal of Pharmaceutics, vol. 85, No. 1-3, pp. 7-17 (Abstract only).

Santoyo et al.; "Penetration Enhancer Effects on the In Vitro Percutaneous Absorption of Piroxicam Through Rat Skin"; Int'l J. Pharm.; 117:219-24 (1995).

Murphy, C. S. et al.; Structure-Function Relationships of Hydroxylated Metabolites of Tamoxifen that Control the Proliferation of Estrogen-Responsive T47D Breast Cancer Cells in Vitro; Molecular Pharmacology 38:737-743 (1990).

Macneil, S. et al.; "Inhibition of melanoma cell/matrix interaction by tamoxifen"; Melanoma Research, 3, pp. 67-74 (1993).

Barrat, J.; "Effet in vivo de l'administration locale de progesterone sur l'activite mitotique des galactophores humains"; J. Gynecol. Obstet. Biol. Reprod., 19, 269-274 (1990).

Kuttenn, F.; "Principe de l'administration percutanée des antiestrogénes en pathologie mammaire"; Contracept, Fertil. Sex., 1991, vol. 19, n°2, pp. 165-171.

Wijayaratne, Ashini J., et al.; "Comparative Analyses of Mechanistic Differences Among Antiestrogens"; Endocrinology, vol. 140, No. 12 (1999).

Jordan, V. Craig; Metabolites of tamoxifen in aminals and man: identification, pharmacology, and significance; Breast Cancer Research and Treatment, 2, 123-138 (1982).

Sauvez, Fabrice et al.; "Cutaneously applied 4-hydroxytamoxifen is not carcinogenic in female rats"; Carcinogenesis vol. 20, No. 5, pp. 843-850 (1999).

Notice of Allowance issued Jun. 13, 2008, in U.S. Appl. No.10/734,638, 7 pages.

Notice of Allowance issued Jun. 24, 2008, in U.S. Appl. No. 10/734,644, 12 pages.

Office Action issued Jul. 9, 2008, in U.S. Appl. No.11/009,390, 16 pages.

* cited by examiner

FIGURE 1: Representation of Tamoxifen Metabolism
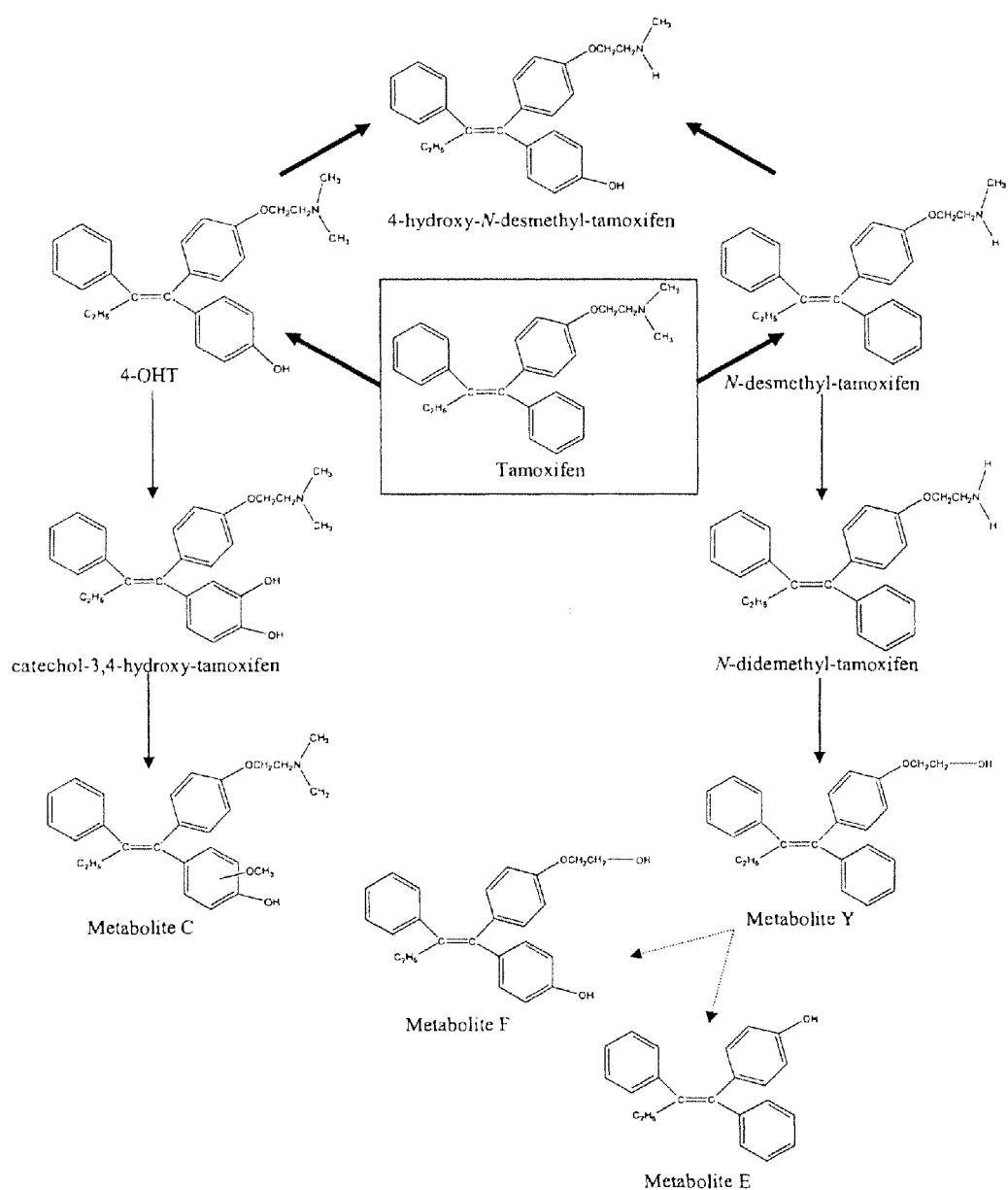

Figure 2: Mean ± SD Plasma Concentration of 4-hydroxy tamoxifen in Healthy Women Following Last Cutaneous Administration (Day 25 of the Second Cycle)
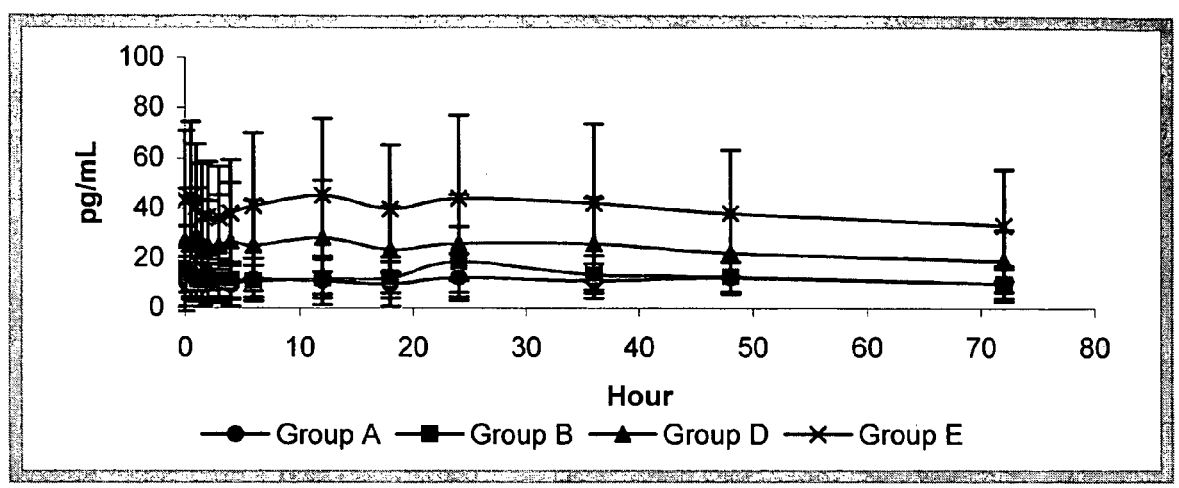

TREATMENT AND PREVENTION OF EXCESSIVE SCARRING WITH 4-HYDROXY TAMOXIFEN

BACKGROUND OF THE INVENTION

The present invention relates to the treatment and prevention of excessive scarring, including keloid and hypertrophic scars, with 4-hydroxy tamoxifen (4-OHT).

Keloid scars, or keloids, are overgrowths of dense fibrous tissue that result from variations in normal wound healing. The dense fibrous tissue of a keloid extends beyond the borders of the original wound, and usually does not regress spontaneously. Thus, keloid scarring is out of proportion to the severity of the inciting wound.

Likewise, hypertrophic scars also are overgrowths of dense fibrous tissue that result from abnormal wound healing. However, hypertrophic scars do not extend beyond the original boundaries of a wound. Also unlike keloids, hypertrophic scars reach a certain size, then stabilize or regress.

The normal wound healing process extends over a one to two year period, and conceptually consists of three distinct stages. The first stage, the inflammatory stage, is intensely degradative. It begins immediately after injury and provides a means to remove damaged tissues and foreign matter from the wound. A few days after injury, the second stage, the proliferation and matrix synthesis stage, begins. During this stage, fibroblasts from surrounding tissues move into the wound and proliferate. The fibroblasts actively produce collagen, which they secrete into the extracellular matrix. Newly synthesized collagen forms cross-linked fibrils, which provide structural integrity to the wound. After several weeks, the final stage, the remodeling stage, begins. During the remodeling stage, the collagen fibrils, which previously were randomly oriented, align in the direction of mechanical tension, providing further mechanical strength to the wound. Upon completion of the entire process, the skin regains its chemical and physical barrier functions.

Six to eight weeks into the normal wound healing process, anabolic and catabolic processes reach an equilibrium. At this time, scar strength is approximately 30-40% that of healthy skin, and scars typically are hyperemic and thickened. Over the next several months, catabolic and anabolic processes abate, and progressive cross-linking of collagen fibers improves the wound's tensile strength. Also, hyperemia and thickness subside until a flat, white, pliable mature scar develops.

Excessive scarring results from an imbalance in the anabolic and catabolic wound healing processes. In the formation of an excessive scar, more collagen is produced than is degraded. As a result, the scar grows larger than is required for wound healing, with an over-production of cells, collagen and proteoglycan. Keloids grow in all directions, become elevated above the skin, and remain hyperemic. The exact mechanisms of excessive scarring are poorly understood, but it is believed that common mechanisms underlie the formation of both keloids and hypertrophic scars. Evidence suggests that increased transforming growth factor β1 (TGF-β1) expression plays a role in excessive scarring. TGF-β1 promotes extracellular matrix production, and is produced at elevated levels by keloid fibroblasts.

Keloids and hypertrophic scars primarily present a cosmetic concern but can cause contractures, which may result in a loss of function if overlying a joint. Additionally, excessive scars can be painful, pruritic and cause a burning sensation. Once keloid lesions occur, they tend to continue growing for weeks to months, even for years. Growth usually progresses slowly, but keloids occasionally enlarge rapidly, even tripling in size within months. Hypertrophic scars tend to stabilize, and regress over time. However, this regression can be quite slow, and often incomplete.

Management of keloids and hypertrophic scars remains a major unsolved clinical problem. Though many forms of treatment have been used, none has proven to be consistently reliable. Current forms of treatment include use of occlusive dressings, compression therapy, intralesional corticosteroid injections, radiation therapy, and surgery.

Occlusive dressings and pressure devices are unpredictable forms of treatment, as a large percentage of patients treated by these means show little or no improvement. Additionally, compliance with these forms of treatment can be impractical. For example, dressings and pressure devices may need to be worn 24 hours per day for up to 12 months. For a scar on a visible or sensitive location, this simply may not be possible.

Intralesional corticosteroids have been the mainstay of keloid treatment. Corticosteroids reduce excessive scarring by reducing collagen synthesis, altering glucosaminoglycan synthesis, and reducing production of inflammatory mediators and fibroblast proliferation during wound healing. However, roughly half of all keloids fail to respond to corticosteroids, and roughly half of the scars that are completely resolved by corticosteroid treatment recur. Additionally, corticosteroid injections can cause several complications, including atrophy, telangiectasia formation, and skin depigmentation.

Radiation therapy may be the only predictably effective treatment for keloids that is presently available. It has the potential to cause cancer, however, and for this reason it is not generally recommended or accepted as a keloid treatment. Moreover, roughly 20 percent of keloids treated by radiation therapy alone recur within one year.

Surgical procedures, including excision, cryosurgery and laser therapy, can effectively remove keloid tissue, and currently are the treatment of choice for hypertrophic scars. However, these techniques often cause tissue trauma that results in further hypertrophic or keloid scars. Indeed, keloids recur in well more than half of patients treated by surgical excision, cryosurgery, and laser therapy. Additionally, these procedures cause pain and present a risk of infection. Cryosurgery also causes skin depigmentation in some patients.

As an alternative keloid treatment, some researchers have proposed using the breast cancer drug tamoxifen (Hu, 1998; Hu 2002). In vitro, tamoxifen inhibits keloid fibroblast proliferation and decreases collagen production. Apparently, tamoxifen effects this inhibition by downregulating TGF-β1 expression, which promotes collagen formation (Chau 1998; Mikulec, 2001).

In vivo use of tamoxifen for treating scars would have drawbacks, however. Tamoxifen is currently available only for oral administration, and its administration by this route poses serious health risks and causes significant unwanted side effects. Tamoxifen potentially impacts on every estrogen receptor in the body, and, as both an agonist and antagonist, provokes a wide range of systemic effects. These effects include the increased risk of endometrial cancer, endometrial hyperplasia and polyps, deep vein thrombosis and pulmonary embolism, changes in liver enzyme levels, and ocular disturbances, including cataracts. Additionally, patients treated with oral tamoxifen reported having hot flashes, vaginal discharge, depression, amenorrhea, and nausea (Fentiman 1986; Fentiman 1988; Fentiman 1989; Ibis 2002). Locally administered tamoxifen, which might pose fewer risks, would eliminate first-pass liver metabolism, which changes tamoxifen into its active metabolites. Without liver metabolism, tamoxifen would be less effective.

Thus, despite the broad array of treatments available, there is no widely accepted and predictably effective means for preventing or treating excessive scars. Therefore, an effective approach to reducing keloid and hypertrophic scars would offer significant benefit if it also provoked few systemic side effects.

SUMMARY OF THE INVENTION

This invention relates to a method for minimizing or preventing excessive scarring, including keloid scars and hypertrophic scars. The method comprises administering an effective amount of 4-hydroxy tamoxifen for a period of time sufficient to minimize the scar or prevent its formation. This treatment approach offers several advantages over other treatments for scars, including (1) few systemic side effects, (2) a better safety profile, (3) easy patient compliance. Additionally, 4-hydroxy tamoxifen can be administered to a wound prophylactically to prevent or minimize excessive scar formation.

In performing the inventive method, 4-hydroxy tamoxifen may be administered by any means that delivers it to a wound or scar tissue in vivo. Preferably, the administration is performed by means that deliver 4-hydroxy tamoxifen locally, limiting systemic exposure to the drug. Examples of such modes include (1) topical administration at the site of a wound or scar, (2) direct injection into a wound or scar site, and (3) implantation of a controlled release polymer or other delivery device that incorporates 4-hydroxy tamoxifen. The inventive method may be performed as the sole form of therapy or prophylaxis, or may be combined with other forms.

A broad range of topical formulations are suitable for performing the invention, but hydroalcoholic solutions and hydroalcoholic gels are preferred. The concentration of 4-hydroxy tamoxifen in these formulations may vary, but a dose should result in local 4-hydroxy tamoxifen concentrations that effectively inhibit fibroblast proliferation and collagen production.

BRIEF DESCRIPTION OF THE FIGURES

FIG. 1 shows the extensive metabolism of tamoxifen in humans.

FIG. 2 shows a plasma concentration-time curve, following cutaneous administration of 4-hydroxy tamoxifen gel to healthy women.

DETAILED DESCRIPTION OF THE PREFERRED EMBODIMENTS

The present inventors have discovered that, by administering 4-hydroxy tamoxifen in a pharmaceutically effective amount, one can treat or prevent excessive scars with fewer unwanted side effects. Thus, the approach of the invention provides a superior safety profile and easier patient compliance, compared to other treatment and prophylactic methods.

According to the present invention, the term "excessive scar" or "excessive scarring" refers to overgrowths of dense fibrous tissue that result from abnormal wound healing. Excessive scars have grown larger than necessary for normal wound healing, and are characterized by overproduction of cells, collagen and/or proteoglycan.

"Keloid scars" are excessive scars in which the dense fibrous tissue extends beyond the borders of the original wound or incision, and does not usually regress spontaneously. Determining whether a scar is a keloid can be difficult, since keloids often superficially resemble other hypertrophic scars. However, keloids have distinguishing histological features. One such feature is the collagen nodule, which contains a high density of fibroblasts and unidirectional collagen fibrils in a highly organized and distinct orientation. Additionally, keloids have a rich vasculature, a high mesenchymal cell density, and a thickened epidermal cell layer.

Skin color and genetics, which correlate with keloid formation, also can aid a determination of whether a scar is a keloid. As many as 16% of black Africans have keloids, while Polynesians, Chinese, Indians and Malaysians have fewer. Whites and albinos have the fewest. Patients with keloid scars tend to have an associated strong family history; both autosomal dominant and autosomal recessive modes of transmission have been reported.

The factors that correlate with keloid formation are helpful as well for determining whether a patient will benefit from prophylactic administration of 4-hydroxy tamoxifen. According to one aspect of the invention, 4-hydroxy tamoxifen is administered to a patient having a wound, when the patient presents an elevated risk for keloid formation. Factors especially useful for determining an elevated risk are an individual and family history of keloids.

"Hypertrophic scars" are excessive scars in which the dense fibrous tissue does not extend beyond the borders of the original wound or incision. They tend to be wider than necessary for normal wound healing to occur. Histologically, hypertrophic scars have more organized collagen fibers than keloids, and scant mucoid matrix. Hypertrophic lesions are characterized by randomly distributed tissue bundles consisting of uniaxially oriented extracellular matrix and cells.

The compound 4-hydroxy tamoxifen, or 1-[4-(2-N-dimethylaminoethoxy)phenyl]-1-(4-hydroxyphenyl)-2-phenyl-but-1-ene, constitutes an active metabolite of the well characterized anti-estrogen compound, tamoxifen. Both E and Z isomers exist, either of which, alone or in combination, are useful according to the present invention. The Z isomer is preferred.

It is well known that 4-hydroxy tamoxifen acts as a selective estrogen receptor modulator (SERM) that exhibits tissue-specificity for estrogen receptive tissues. Studies have shown that 4-hydroxy tamoxifen can regulate the transcriptional activity of estrogen-related receptors, which may contribute to its tissue-specific activity. In vitro, 4-hydroxy tamoxifen exhibits more potency than tamoxifen, as measured by binding affinity to estrogen receptors, or ERs, and a binding affinity similar to estradiol for estrogen receptors (Robertson et al., 1982; Kuiper et al., 1997). Z-4-hydroxy tamoxifen inhibits the growth in culture of normal human epithelial breast cells 100 fold more than Z-tamoxifen (Malet et al., 1988).

Although 4-hydroxy tamoxifen is a tamoxifen metabolite, its usefulness for treating and preventing excessive scars is not presaged by previous experience with tamoxifen itself. Tamoxifen is extensively metabolized in humans, as shown in FIG. 1. Thus, its action in vivo is the net result of individual actions by the parent compound and its metabolite compounds competing for the occupation of receptors within target tissues. For example, see Jordan, 1982. Each of these compounds manifests different and unpredictable biological activities in different cells, determined in part by each compound's individual effect on receptor conformation. That is, receptor binding of each compound generates a unique receptor-ligand conformation that recruits different cofactors, and results in varying pharmacologies for the different compounds (Wijayaratne et al., 1999; Giambiagi et al., 1988).

Several examples of these varying effects have been documented. For instance, tamoxifen but not 4-hydroxy tamoxifen is a potent rat liver carcinogen. (Carthew et al., 2001; Sauvez et al., 1999). Additionally, tamoxifen but not 4-hydroxy tamoxifen initiates apoptosis in p53(−) normal human mammary epithelial cells (Dietze et al., 2001). By contrast, 4-hydroxy tamoxifen exhibits a significant inhibitory effect on estrone sulphatase activity in mammary cancer cell lines, while tamoxifen has little or no effect in this regard (Chetrite et al., 1993).

Methods for preparing 4-hydroxy tamoxifen are well known. For example, U.S. Pat. No. 4,919,937 to Mauvais-Jarvis et al. describes a synthesis derived from Robertson and Katzenellenbogen, 1982. That synthesis occurs in several stages:

- Stage 1—Reaction between 4-(β-dimethylaminoethoxy)-α-ethyldeoxybenzoin and p-(2-tetrahydropyranyloxy) phenylmagnesium bromide;
- Stage 2—Separately from stage 1, formation of 1-(4-hydroxyphenyl)-2-phenyl-1-butanone by hydroxylation of 1,2-diphenyl-1-butanone;
- Stage 3—Reaction between the products of stages 1 and 2 to form 1-(4-dimethylaminoethoxyphenyl)-1-[p-2-tetrahydropyranyloxy)phenyl]-2-phenylbutan-1-ol;
- Stage 4—Dehydration with methanol/hydrochloric acid produces 1-[p-(β-dimethylaminoethoxy)phenyl]-Z-1-(p-hydroxyphenyl)-2-pheny-1-but-1-ene=4-OH-tamoxifen, a mixture of E and Z isomers;
- Stage 5—Separation of the E and Z isomers by chromatography and crystallization to constant specific activity.

According to the present invention, 4-hydroxy tamoxifen may be administered in any dosage form and via any system that delivers the active compound to a wound or scar in vivo. Preferably, the administration is performed by a means that delivers 4-hydroxy tamoxifen locally, limiting systemic exposure to the drug. For example, 4-hydroxy tamoxifen, alone or in combination with a pharmaceutically acceptable vehicle, can be topically applied to the surface of a wound or scar site, can be injected into a wound or scar site, or can be incorporated in to a controlled release polymer and surgically implanted in a region to be treated. The optimal method of administering an acceptable dose to minimize scarring will depend upon the location of the scar and the extent of scarring.

Preferably, the 4-hydroxy tamoxifen is delivered topically, such as by "cutaneous administration," a phrase that denotes any mode of delivering a drug from the surface of a patient's skin, through the stratum corneum, epidermis, and dermis layers, and into the microcirculation. This is typically accomplished by diffusion down a concentration gradient. The diffusion may occur via intracellular penetration (through the cells), intercellular penetration (between the cells), transappendageal penetration, (through the hair follicles, sweat, and sebaceous glands), or any combination of these. Topical administration offers the distinct advantage of being non-invasive.

A proper dose for administration should result in local 4-hydroxy tamoxifen concentrations that effectively inhibit fibroblast proliferation and collagen production, without causing significant side effects. Although the invention is not constrained to any particular theory, clinically significant side effects of anti-estrogen agents occur when the agents displace estradiol in non-target tissues. Because 4-hydroxy tamoxifen and estradiol have similar binding affinities for estrogen receptors, a competition between them for receptor binding would be approximately equal when the concentration of each compound approximates that of the other. If the 4-hydroxy tamoxifen concentration exceeds the estradiol concentration, then the former will be bound preferentially to the estrogen receptors, and vice versa.

Accordingly, doses of 4-hydroxy tamoxifen that result in plasma concentrations less than the estradiol concentration are preferred. The daily doses to be administered can initially be estimated based upon the absorption coefficients of 4-hydroxy tamoxifen, the tissue concentration that is desired, and the plasma concentration that should not be exceeded. By administering 4-hydroxy tamoxifen locally, high concentrations can be achieved in the target tissues without simultaneously raising 4-hydroxy tamoxifen plasma levels to a point where significant systemic competition for estradiol receptors occurs. Of course, the initial dose may be optimized in each patient, depending on individual responses.

In a topical formulation, doses on the order of 0.25 to 3 ug of 4-hydroxy tamoxifen/$cm^2$/day should achieve the desired result, with doses of about 0.5 to 2.5 ug/$cm^2$/day being preferred. Doses of about 1.0 and 2.0 ug/$cm^2$/day are more highly preferred.

Cutaneous administration can be accomplished mainly in two different ways: (i) by mixing a therapeutically active compound or its non-toxic pharmaceutically acceptable salt with suitable pharmaceutical carriers and, optionally, penetration enhancers to form ointments, emulsions, lotions, solutions, creams, gels or the like, where an amount of said preparation is applied onto a wound or scar site, or (ii) by incorporating the therapeutically active substance into patches or transdermal delivery systems according to known technology.

The effectiveness of cutaneous drug administration depends on many factors, including drug concentration, surface area of application, time and duration of application, skin hydration, physicochemical properties of the drug, and partitioning of the drug between the formulation and the skin. Drug formulations intended for cutaneous use take advantage of these factors to achieve optimal delivery. Such formulations often contain penetration enhancers that improve cutaneous absorption by reducing the resistance of the stratum corneum by reversibly altering its physiochemical properties, changing hydration in the stratum corneum, acting as co-solvent, or changing the organization of lipids and proteins in the intercellular spaces. Such enhancers of cutaneous absorption include surfactants, DMSO, alcohol, acetone, propyleneglycol, polyethylene glycol, fatty acids, fatty alcohols and related molecules, pyrrolidones, urea, and essential oils. In addition to chemical enhancers, physical methods can increase cutaneous absorption. For example, occlusive bandages induce hydration of the skin. Other physical methods include iontophoresis and sonophoresis, which use electrical fields and high-frequency ultrasound, respectively, to enhance absorption of drugs that are poorly absorbed due to their size and ionic characteristics.

The many factors and methods relating to cutaneous drug delivery are reviewed in REMINGTON: THE SCIENCE AND PRACTICE OF PHARMACY, Alfonso R. Gennaro (Lippincott Williams & Wilkins, 2000), at pages 836-58, and in PERCUTANEOUS ABSORPTION: DRUGS COSMETICS MECHANISMS METHODOLOGY, Bronaugh and Maibach (Marcel Dekker, 1999). As these publications evidence, those in the pharmaceutical field can manipulate the various factors and methods to achieve efficacious cutaneous delivery.

4-Hydroxy tamoxifen is a large and very lipophilic molecule; hence, without assistance from penetration enhancers it poorly penetrates the skin. Accordingly, formulations of 4-hydroxy tamoxifen used in the present invention preferably contain one or more penetration enhancers. Alcohols are preferred enhancers because 4-hydroxy tamoxifen is soluble in alcohol. Isopropyl myristate also is a preferred enhancer.

For cutaneous administration, 4-hydroxy tamoxifen may be delivered in an ointment, cream, gel, emulsion (lotion), powder, oil or similar formulation. To this end, the formulation may comprise customary excipient additives, including vegetable oils such as almond oil, olive oil, peach kernel oil, groundnut oil, castor oil and the like, animal oils, DMSO, fat and fat-like substances, lanolin lipoids, phosphatides, hydrocarbons such as paraffins, petroleum jelly, waxes, detergent emulsifying agents, lecithin, alcohols, carotin, glycerol, glycerol ethers, glycols, glycol ethers, polyethylene glycol, polypropylene glycol, non-volatile fatty alcohols, acids, esters, volatile alcoholic compounds, urea, talc, cellulose derivatives, and preservatives.

For practicing the present invention, preferred formulations contain 4-hydroxy tamoxifen in a hydroalcoholic gel. The amount of 4-hydroxy tamoxifen per 100 grams of gel may range from about 0.001 gram to about 1.0 gram. Preferably, it ranges from about 0.01 gram to about 0.1 gram. Table 1 describes the composition of two highly preferred 4-hydroxy tamoxifen gel formulations.

TABLE 1

Composition of 4-Hydroxy Tamoxifen Gel Formulations

| | Quantity per 100 g of gel | |
|---|---|---|
| Ingredient | 20 mg 4-OHT Gel | 57 mg 4-OHT Gel |
| 4-Hydroxy Tamoxifen | 0.02 g | 0.057 g |
| Absolute Ethyl Alcohol, EP, USP-NF | 66.5 g | 66.5 g |
| Isopropyl myristate, EP, USP-NF | 1 g | 1 g |
| Hydroxypropylcellulose, EP, USP-NF | 1.5 g | 1.5 g |
| Phosphate Buffer (pH 7, diluted 1:4), EP | q.s. 100 g | q.s. 100 g |

According to the present invention, 4-hydroxy tamoxifen also may be delivered via a transdermal patch. In one embodiment, the patch comprises a reservoir for the 4-hydroxy tamoxifen formula. The patch may comprise (a) a solution-impermeable backing foil, (b) a layer-like element having a cavity, (c) a microporous or semi-permeable membrane, (d) a self-adhesive layer, and (e) optionally, a removable backing film. The layer-like element having a cavity may be formed by the backing foil and the membrane. Alternatively, the patch may comprise (a) a solution-impermeable backing foil, (b) an open-pored foam, a closed-pore foam, a tissue-like layer or a fibrous web-like layer as reservoir, (c) if the layer according to (b) is not self-adhesive, a self-adhesive layer, and (d) optionally a removable backing film.

It is contemplated that the administration of 4-hydroxy tamoxifen may be combined with other keloid therapies. According to the present invention, therefore, administration of 4-hydroxy tamoxifen may be accompanied by the use of occlusive dressings, compression therapy, intralesional corticosteroid injections, radiation therapy, and surgery, including cryotherapy and laser therapy.

Reference to the following, illustrative examples will help to provide a more complete understanding of the invention.

EXAMPLE 1

Demonstration of Cutaneous 4-Hydroxy Tamoxifen Delivery

Four patients with breast cancer received [$^3$H]-4-hydroxy tamoxifen in an alcoholic solution applied directly to the breasts at specified intervals between 12 hours to 7 days prior to surgery to excise diseased tissue. After surgery, both the excised tissue and the normal breast tissue surrounding the tumor contained radioactivity (Kuttenn et al., 1985).

In a follow-up study, 9 of 12 patients scheduled for surgical excision of hormone-dependent breast cancer received Z-[$^3$H]-4-hydroxy tamoxifen (80 µCi) in a 60% alcoholic solution, and 3 patients received Z-[$^3$H]-tamoxifen (80 µCi) for comparison. The patients received [$^3$H]-labeled drug applied directly on the affected breasts at specified intervals ranging from 12 hours to 7 days before surgery to excise diseased tissue. Breast tissue from three regions: the tumor, tissue immediately surrounding the tumor, and normal tissue, was excised and immediately frozen in liquid nitrogen. Additionally, plasma and urine samples were obtained at scheduled intervals and frozen until analysis.

Table 2 shows results from the analyses performed. 4-Hydroxy tamoxifen concentrated predominantly in the cytosolic and nuclear fractions of breast tissue, where estrogen receptors are present. In these intracellular sites, 4-hydroxy tamoxifen remained unmetabolized except for limited isomerization from the Z to the E form. Retention in the breast lasted approximately 4 days in the 4-hydroxy tamoxifen group, but was shorter and far weaker in the tamoxifen group.

TABLE 2

[$^3$H]-4-Hydroxy Tamoxifen and Metabolites Identified in Breast Tumor Tissue Following Cutaneous Administration of Z-[$^3$H]-4-Hydroxy Tamoxifen to the Affected Breast

| | % Metabolites in Breast Tissue | | | | |
|---|---|---|---|---|---|
| Metabolites | 12 hr[1] | 24 hr | 36 hr | Day 4 | Day 7 |
| 4-Hydroxy Tamoxifen | 97 | 94 | 78 | 70 | 65 |
| N-Desmethyl-4-Hydroxy Tamoxifen | 2 | 4 | 14 | 20 | 16 |
| Bisphenol | 1 | 2 | 3 | 8 | 8 |
| N-Desmethyl tamoxifen | | | <1 | <1 | 3-4 |
| Tamoxifen | | | | <1 | 2 |

[1]Time after administration of Z-[$^3$H]-4-hydroxy tamoxifen

The percentage of radioactivity identified as [$^3$H]-4-hydroxy tamoxifen in breast tissue after cutaneous administration decreased slowly over seven days (from 97% to 65%). During this period a progressive isomerization of the Z isomer into the E isomer occurred, with similar percentages observed at day 7 (32% and 33%).

The radioactivity in blood due to [$^3$H]-4-hydroxy tamoxifen increased gradually, with a plateau from days 4 to 6. This contrasts with [$^3$H]-tamoxifen, which rapidly appeared in the blood, plateauing at 2 days. At 36 hours following cutaneous [$^3$H]-4-hydroxy tamoxifen administration, only 0.5% of the radioactivity administered showed in the blood.

Marked metabolism of 4-hydroxy tamoxifen occurred in blood, in contrast to the near absence of such metabolism in the breast tissue. At 24 hours after administration, 68% of radioactivity in blood represented 4-hydroxy tamoxifen, 18% represented N-desmethyl-4-hydroxy tamoxifen, and 11% represented bisphenol.

Peak urinary elimination occurred at a later time following cutaneous administration of 4-hydroxy tamoxifen compared to cutaneous tamoxifen. Following application of 4-hydroxy tamoxifen, a progressive increase of metabolites, mostly N-desmethyl-4-hydroxy tamoxifen and bisphenol, was observed in the urine.

This example demonstrates that cutaneous application of 4-hydroxy tamoxifen results in a substantial and lasting local tissue concentration of the drug, with minimal metabolism, stable and very low plasma concentrations, and slow elimination via the urine.

EXAMPLE 2

Demonstration of the Pharmacokinetics and Pharmacodynamics of Cutaneously Administered 4-OH-Tamoxifen Compared to 20 mg of Oral Tamoxifen This study compared the tissue and plasma concentrations of 4-hydroxy tamoxifen after cutaneous administration via a hydroalcoholic gel with tissue and plasma concentrations of 4-hydroxy tamoxifen after oral administration of tamoxifen. (Pujol et al.).

Thirty-one patients scheduled for breast cancer surgery were randomly assigned to 1 of 5 groups. They received treatment with either oral tamoxifen or cutaneous 4-hydroxy tamoxifen as outlined in Table 3. Treatment was daily and lasted for 3-4 weeks prior to surgery. The study evaluated three different doses of 4-hydroxy tamoxifen (0.5, 1, or 2 mg/day) and two areas of application (either to both breasts or to a large surface of skin including arms, forearms, and shoulders). One group of patients received 20 mg/day (10 mg b.i.d.) of oral tamoxifen (Nolvaldex®).

TABLE 3

Treatment Groups

| Group | N | Drug | Application Site | Dose mg/breast/day | Total Daily Dose (mg/day) |
|---|---|---|---|---|---|
| 1 | 6 | PO tamoxifen | — | — | 20[a] |
| 2 | 6 | 4-OHT gel | both breasts | 0.25 | 0.5 |
| 3 | 5 | 4-OHT gel | both breasts | 0.50 | 1 |
| 4 | 5 | 4-OHT gel | arms, forearms, and shoulders | — | 1 |
| 5 | 6 | 4-OHT gel | arms, forearms, and shoulders | — | 2[b] |

[a]10 mg b.i.d.
[b]divided into 2 daily applications; 1 mg in the morning and 1 mg in the evening The 4-hydroxy tamoxifen gel (20 mg of 4-hydroxy tamoxifen/100 g of hydroalcholic gel; Besins-Iscovesco Laboratories) was packaged in a pressurized dose-metering pump that delivered 1.25 g of gel/metered dose (i.e., 0.25 mg of 4-hydroxy tamoxifen/dose).

During surgery, two samples (1 cm$^3$ each) of breast tissue were excised, one tumoral and the other macroscopically normal. They were immediately frozen in liquid nitrogen until assayed. Blood samples were obtained on the day of and the day prior to surgery. All tissue and plasma samples were analyzed for 4-hydroxy tamoxifen concentration by gas chromatograph/mass spectrometry (GC-MS).

Pre and post-treatment blood samples were assayed for complete blood counts (CBC), bilirubin, serum glutamic-pyruvic transaminase (SGPT), serum glutamic-oxaloacetic transaminase (SGOT), alkaline phosphatase, creatinine, estradiol, follicle-stimulating hormone (FSH), lutenizing hormone (LH), sex hormone-binding globulin (SHBG), cholesterol, high-density lipoprotein (HDL), low-density lipoprotein (LDL), triglycerides, fibrinogen, and anti-thrombin III.

Table 4 below summarizes the concentration of 4-hydroxy tamoxifen found in breast tissue and plasma. Normal and tumor breast tissues contained similar concentrations of 4-hydroxy tamoxifen in all five treatment groups. 4-hydroxy tamoxifen concentrated at higher amounts in breast tissue when the gel was applied directly to the breasts, rather than to other large skin surfaces.

Side effects did not pose a significant problem. Cutaneous treatment did not cause any local irritation. One woman in Group 2 (0.5 mg/day of 4-hydroxy tamoxifen gel) reported dizzy spells, cystitis, and mild vaginitis occurring on the seventh day of treatment. One woman in Group 1 (oral tamoxifen) reported hot flashes and mild vaginitis on the fifth day of treatment.

No differences existed between the pre- and post treatment blood samples for any of the hematology or serum chemistry evaluations in the patients who received 4-hydroxy tamoxifen gel. However, a statistically significant decrease in anti-thrombin III and fibrinogen and a statistically significant increase in platelet and lymphocyte counts were observed in the oral tamoxifen group, consistent with the biologic effects of this drug observed in other studies.

TABLE 4

Concentrations of 4-hydroxy tamoxifen

Mean ± SD 4-hydroxy tamoxifen (Range)

| Group | N | Day Pre-Surgery | Day of Surgery | Plasma Concentrations (pg/mL) Normal Tissue (pg/g) | Tumor (pg/g) |
|---|---|---|---|---|---|
| 1 | 6 | 2326 ± 585 (1371-2959)[a] | 2317 ± 1098 (881-4176) | 10215 ± 2151 (5873-11511) | 12453 ± 3751 (9568-18904)[a] |
| 2 | 6 | 0 (0-0)[a] | 17 ± 27 (0[c]-61) | 353 ± 513 (0[d]-1317) | 1447 ± 2673 (0[f]-6889) |
| 3 | 5 | 164 ± 131 (29-279)[b] | 62 ± 71 (28-190) | 1112 ± 1125 (197-2979) | 1877 ± 2472 (345-6211) |
| 4 | 5 | 94 ± 76 (35-201)[b] | 13 ± 29 (0[c]-65) | 140 ± 130 (0[e]-270) | 552 ± 357 (271-1150) |
| 5 | 6 | 78 ± 138 (0[e]-284)[b] | 73 ± 114 (0[c]-244) | 992 ± 2195 (0[d]-5462) | 224 ± 312 (0[d]-799) |

[a]n = 5
[b]n = 4
[c]Four patients had undetectable levels of 4-hydroxy tamoxifen (LOQ = 20 pg/ml).
[d]Three patients had undetectable levels of 4-hydroxy tamoxifen.
[e]2 patients had undetectable levels of 4-hydroxy tamoxifen
[f]1 patient had undetectable levels of 4-hydroxy tamoxifen

EXAMPLE 3

Demonstration of Tolerance and Pharmacokinetics of Cutaneously Administered 4-OH-Tamoxifen in Healthy Women This study demonstrates the tolerance and pharmacokinetics of topically applied 4-hydroxy tamoxifen gel in healthy premenopausal women, aged 18-45. Each participant applied the gel daily for the duration of two menstrual cycles.

Three doses and two gel concentrations were tested, as summarized in Table 5. For Groups A-C, the gel, containing 20 mg of 4-hydroxy tamoxifen/100 g, was dispensed from a pressurized dose-metering pump that delivered 0.25 mg of 4-hydroxy tamoxifen/dose. The study of Group C was suspended because the quantity of gel was too large to be applied to a single breast. Groups D and E received a more concentrated gel that contained almost 3 times as much 4-hydroxy tamoxifen: 57 mg of 4-hydroxy tamoxifen/100 g, or 50 mg of 4-hydroxy tamoxifen/100 mL of gel. This more concentrated gel also was delivered by a dose-metering pump that supplied 0.25 mg of 4-hydroxy tamoxifen/dose.

TABLE 5

Treatment Groups

| Group | N | Dose (mg/day) | Gel Concentration (mg of 4-OHT/g of gel) | Treatment |
|---|---|---|---|---|
| A | 12 | 0.5 | 20 mg/100 g | 1 metered dose/breast/day |
| B | 8 | 1 | 20 mg/100 g | 2 metered doses/breast/day |
| C | 2 | 2 | 20 mg/100 g | study was interrupted |
| D | 12 | 1 | 57 mg/100 g | 2 metered doses/breast/day |
| E | 12 | 2 | 57 mg/100 g | 4 metered doses/breast/day |

At the end of a menstrual cycle, each patient received a single dose, after which serial blood samples were collected at 0, 0.5, 1, 1.5, 2, 3, 4, 6, 12, 18, 24, 36, 48, and 72 hours.

On the first day of the following menstruation, treatment, which consisted of daily application of the gel over two menstrual cycles, began. Blood samples were collected 24 hours following the morning application of gel on days 7, 20 and 25 of the first and second cycles. On the last day of administration, day 25 of the second menstrual cycle, serial blood samples were collected prior to application and at 0.5, 1, 1.5, 2, 3, 4, 6, 12, 18, 24, 36, 48, and 72 hours after application of the gel. The samples were analyzed for 4-hydroxy tamoxifen, estradiol, progesterone, FSH and LH.

Plasma concentrations of 4-hydroxy tamoxifen remained detectable 72 hours after the last gel application. Therefore, to ensure that data points were obtained until 4-hydroxy tamoxifen became undetectable in the blood, additional blood samples were collected from some participants at intervals up to 92 days following the last application of gel.

Table 6 displays the mean±standard deviation (SD) plasma concentrations of 4-hydroxy tamoxifen, with ranges in parentheses. A single 0.5 mg dose did not produce detectable plasma concentrations of 4-hydroxy tamoxifen, but 6 of 12 patients had detectable plasma concentrations (>5 pg/mL) after a single dose of 1 mg.

TABLE 6

Mean ± SD Plasma Concentrations of 4-Hydroxy Tamoxifen in Healthy Women Following Daily Cutaneous Administration for Two Menstrual Cycles

| | | Time after | Mean ± SD (Range is indicated in parenthesis) in pg/mL | | | |
|---|---|---|---|---|---|---|
| Cycle | Day | Application (hr) | 0.5 mg/day (n = 12)[1] | 1 mg/day (n = 8)[1] | 1 mg/day (n = 12)[2] | 2 mg/day (n = 12)[2] |
| First | 1 | 0 | (0-17.2) | (0-13.9) | (0-9.5) | (0-0) |
| | 7 | 24 | 6.4 ± 5.6 (<LOQ-16.8) | 15.2 ± 9.7 (<LOQ-26.8) | 14.4 ± 13.1 (<LOQ-37.9) | 26.9 ± 18.2 (8.9-71.3) |
| | 20 | 24 | 13.6 ± 7.9 (<LOQ-25.9) | 17.3 ± 9.5 (<LOQ-29.8) | 18.1 ± 15.8 (<LOQ-44.5) | 44.0 ± 29.2 (10.5-117.5) |
| | 25 | 24 | 23.9 ± 23.4 (<LOQ-73.1) | 15.5 ± 6.6 (6.4-25.0) | 19.8 ± 16.2 (6.2-57.0) | 45.4 ± 31.0 (17.9-120.1) |
| Second | 7 | 24 | 25.2 ± 16.1 (6.5-61.7) | 17.4 ± 11.2 (5.7-39.6) | 22.2 ± 16.4 (9.0-64.4) | 42.2 ± 24.8 (18.2-98.0) |
| | 20 | 24 | 15.7 ± 14.0 (<LOQ-52.3) | 14.8 ± 6.5 (5.4-24.8) | 24.4 ± 20.1 (<LOQ-65.4) | 38.9 ± 27.1 (18.7-119.7) |
| | 25 | 0[3] | 10.8 ± 9.9 (<LOQ-36.4) | 15.7 ± 17.1 (<LOQ-56.4) | 27.2 ± 20.8 (8.0-72.1) | 43.2 ± 27.7 (16.9-120.3) |
| | | 0.5 | 10.9 ± 7.4 (<LOQ-26.0) | 13.5 ± 9.1 (<LOQ-27.7) | 25.9 ± 18.7 (8.7-69.2) | 44.5 ± 29.9 (13.6-124.5) |
| | | 1 | 10.4 ± 7.8 (<LOQ-26.7) | 10.8 ± 6.6 (<LOQ-23.8) | 28.7 ± 19.5 (8.8-69.2) | 40.5 ± 25.1 (14.2-106.7) |
| | | 1.5 | 9.0 ± 8.2 (<LOQ-25.1) | 11.8 ± 8.0 (<LOQ-23.6) | 25.6 ± 17.8 (7.5-67.0) | 36.8 ± 21.1 (15.9-90.0) |
| | | 2 | 11.8 ± 9.5 (<LOQ-26.9) | 10.7 ± 6.9 (<LOQ-24.7) | 25.1 ± 18.0 (6.9-67.3) | 36.8 ± 21.6 (13.0-83.7) |
| | | 3 | 10.0 ± 7.9 (<LOQ-23.1) | 11.4 ± 7.9 (<LOQ-28.1) | 24.8 ± 20.5 (9.0-69.9) | 36.1 ± 20.6 (11.9-89.4) |
| | | 4 | 9.2 ± 8.3 (<LOQ-25.3) | 11.2 ± 7.3 (<LOQ-25.7) | 26.8 ± 23.3 (6.4-78.1) | 38.1 ± 21.2 (16.5-92.0) |
| | | 6 | 11.4 ± 8.5 (<LOQ-26.6) | 10.7 ± 6.4 (<LOQ-22.8) | 25.0 ± 18.2 (9.0-65.3) | 41.0 ± 29.1 (14.0-123.8) |
| | | 12 | 11.0 ± 9.7 (<LOQ-29.1) | 11.8 ± 7.8 (<LOQ-28.1) | 28.3 ± 22.9 (6.4-74.6) | 45.1 ± 30.6 (18.7-126.8) |
| | | 18 | 9.7 ± 8.8 (<LOQ-24.9) | 12.2 ± 8.3 (<LOQ-29.6) | 23.4 ± 17.4 (8.1-57.9) | 39.8 ± 25.5 (16.0-107.3) |
| | 26 | 24 | 12.4 ± 9.4 (<LOQ-34.4) | 18.6 ± 14.2 (<LOQ-40.1) | 26.0 ± 19.6 (8.9-61.9) | 44.0 ± 33.0 (15.8-132.5) |
| | | 36 | 10.9 ± 6.9 (5.0-25.8) | 13.4 ± 7.5 (<LOQ-25.4) | 25.7 ± 18.4 (8.8-61.3) | 42.1 ± 31.5 (15.1-129.3) |
| | 27 | 48 | 12.1 ± 6.5 (4.8-26.6) | 12.5 ± 6.0 (<LOQ-19.6) | 22.0 ± 16.0 (5.6-50.2) | 38.1 ± 25.3 (17.5-110.0) |

TABLE 6-continued

Mean ± SD Plasma Concentrations of 4-Hydroxy Tamoxifen in Healthy Women Following Daily Cutaneous Administration for Two Menstrual Cycles

| | | Time after Application (hr) | Mean ± SD (Range is indicated in parenthesis) in pg/mL | | | |
|---|---|---|---|---|---|---|
| Cycle | Day | | 0.5 mg/day (n = 12)[1] | 1 mg/day (n = 8)[1] | 1 mg/day (n = 12)[2] | 2 mg/day (n = 12)[2] |
| | 28 | 72 | 9.9 ± 7.1 (<LOQ-22.3) | 9.9 ± 5.8 (<LOQ-19.6) | 18.9 ± 12.4 (5.6-37.8) | 33.2 ± 22.2 (17.7-98.0) |
| | | +5 days | — | 5.8 ± 5.2 (<LOQ-12.4) | 11.4 ± 8.2 (<LOQ-25.8) | 20.4 ± 17.3 (9.1-71.6) |
| | | +8 days | <LOQ | (<LOQ-17.4) | (0-14.8) | 10.8 ± 13.4 (<LOQ-52.0) |
| | | +12 days | (maximum 9.09) | (<LOQ-7.0) | (0-<LOQ) | (0-30.4) |
| | | +20 days | 0 | <LOQ | (0-<LOQ) | (0-<LOQ) |

[1]Gel concentration was 20 mg of 4-hydroxy tamoxifen per 100 g of gel.
[2]Gel concentration was 57 mg of 4-hydroxy tamoxifen per 100 g of gel.
[3]Timepoint 0 is 24 hours after the application on Day 24 and prior to the final application on Day 25.
LOQ = limit of quantification (<5 pg/mL)

FIG. 2 shows a plasma concentration-time curve, following the last administration on day 25 of the second menstrual cycle. Table 7 shows mean pharmacokinetic parameters that relate to the last administration, on day 25 of the second menstrual cycle.

TABLE 7

Mean Pharmacokinetic Parameters of 4-Hydroxy Tamoxifen in Healthy Women Following the Last Administration

| | Mean ± SD (Range is indicated in parenthesis) | | | |
|---|---|---|---|---|
| Parameter | 0.5 mg/day (n = 12)[a] | 1 mg/day (n = 8)[a] | 1 mg/day (n = 12)[b] | 2 mg/day (n = 12)[b] |
| $C_{max}$ (pg/mL) | 17.0 ± 8.5 (7.6-34.4) | 21.0 ± 14.0 (<LOQ-40.1) | 35.1 ± 22.4 (9.9-78.1) | 51.6 ± 31.7 (22.1-132.5') |
| $t_{max}$ (hr) | 40 ± 81 (0.5-288) | 24 ± 18 (0.5-48) | 12.8 ± 14.9 (1-36) | 11.8 ± 12.3 (0.5-36) |
| $t_{1/2}$ (hr) | — | — | (58-118) | (49-101) |
| $AUC_{0-24}$ (pg · hr/mL) | 256.3 ± 205.3 (24.6-651.1) | 300.9 ± 190.8 (0-693.6) | 619 ± 466 (187-1522) | 998 ± 653 (424-2778) |
| $C_{av} = AUC_{0-24}/24$ (pg/mL) | 10.7 ± 8.5 (1.0-27.1) | 12.5 ± 7.9 (0-28.9) | 25.8 ± 19.4 (7.8-63.4) | 41.6 ± 27.2 (17.7-115.8) |
| T(1stC < LOQ) (hr) | — | 274 ± 141 (144-480) | 236 ± 72 (144-384) | 326 ± 97 (192-480) |

[a]Gel concentration was 20 mg of 4-hydroxy tamoxifen per 100 g of gel.
[b]Gel concentration was 57 mg of 4-hydroxy tamoxifen per 100 g of gel.
$AUC_{0-24}$ = area under the concentration-time curve for 0-24 hours;
$C_{av}$ = Calculation of area under the curve over 24 hours ($AUC_{0-24}$) divided by 24 hours;
$C_{max}$ = maximal concentration in plasma;
$t_{1/2}$ = half-life;
T(1stC < LOQ) = first timepoint at which the plasma concentration was below the limit of quantification;
$t_{max}$ = time of maximal concentration in plasma.

The data are consistent with a dose response across the three doses tested (0.5, 1, and 2 mg). The more concentrated gel was better absorbed, by approximately double, than the less concentrated gel, based on AUC and $C_{av}$.

Biological tolerance was excellent in all 36 patients. The treatment did not affect FSH, LH, estradiol, or progesterone hormone levels during the menstrual cycles. Moreover, echographic examination of the ovaries at the end of treatment was normal in all patients, showing normal sized developing follicles. One patient developed an allergic reaction to the gel, and 10 reported facial acne.

In summary, this study indicates that the exposure to 4-hydroxy tamoxifen after topical application increases with dose, that plasma concentrations of 4-hydroxy tamoxifen are lower than typical estradiol concentrations (80 pg/mL), and that there is no detectable laboratory or clinical evidence of systemic effects.

EXAMPLE 4

Study to Demonstrate Efficacy for Cutaneous 4-Hydroxy Tamoxifen in Treating Keloid Scars The primary objective of this study is to demonstrate that 4-hydroxy tamoxifen, when administered cutaneously, effectively treats keloid scars.

Patients diagnosed with a keloid scar receive either placebo or 4-hydroxy tamoxifen gel for a period of 6 months. For the treatment group, between 1 and 2 mg gel g/cm² (57 mg 4-OHT/100 g gel) is administered twice per day, that is between 0.5 and 1 µg 4-OHT/cm². Multiple clinical efficacy endpoints are evaluated: (1) each patient assesses pain, discomfort, and itching due to the keloid, (2) scars are staged using the Vancouver scar scale, (3) biopsies are compared at baseline and after 6 months of treatment by histological analysis, (4) molecular analysis of TGF-β isoform and collagen expression are performed. Patients in the treatment group show statistically significant improvement in the endpoints versus patients in the placebo group.

CITED PUBLICATIONS

Bronaugh and Maibach, Percutaneous Absorption: Drugs Cosmetics Mechanisms Methodology, Marcel Dekker 1999.

Carthew, P., P. N. Lee, R. E Edwards, R. T. Heydon, B. M. Nolan, E. A. Martin, Cumulative exposure to tamoxifen: DNA adducts and liver cancer in the rat, Arch Toxicol, 75: 375-80 (2001).

Chetrite, G., C. Varin, L. Delalonde, J. R. Pasqualini, Effect of promegestone, tamoxifen, 4-hydroxytamoxifen and ICT 164,384 on the oestrone sulphatase activity of human breast cancer cells, Anticancer Res, 13(4) 931-4 (July-August 1993).

Chau, D., J. S. Mancoll, S. Lee, J. Zhao, L. G. Phillips, G. I. Gittes, M. T. Longaker, Tamoxifen downregulates TGB-beta production in keloid fibroblasts, Ann. Plast. Surg., 40(5): 490-3 (1998).

Dietze, E. C., L. E. Caldwell, S. L. Grupin, M. Mancini, and V. L. Seewald, Tamoxifen, but not 4-hydroxytamoxifen initiates apoptosis in p53(−) normal human mammary epithelial cells by inducing mitochondrial depolarization, J. Biol. Chem., 276(7): 5384-94 (Feb. 16, 2001).

Fentiman, I. S., Tamoxifen and mastalgia. An emerging indication, Drugs 32: 477-80 (1986).

Fentiman, I. S., M. Caleffi, H. Hamed, and M. A. Chaudary, Dosage and duration of tamoxifen treatment for mastalgia: a controlled trial, British Journal of Surgery 75: 845-46 (1988).

Fentiman, I. S., M. Caleffi, H. Hamed, and M. A. Chaudary, Studies of tamoxifen in women with mastalgia, British Journal of Clinical Practice, Supplement 68, 43(11): 34-36 (1989))

Giambiagi, N. and J. R. Pasqualini, Immunological differences between the estradiol-, tamoxifen and 4-hydroxy-tamoxifen estrogen receptor complexes detected by two monoclonal antibodies, J. Steroid Biochem, 30(1-6): 213-7 (1988).

Hu, D., M. A. Hughes, G. W. Cherry, Topical tamoxifen—a potential therapeutic regimen in treating excessive dermal scarring?, Br. J. Plast. Surg., 50(6): 462-9 (1998).

Hu, D., X. Zhu, M. Xu, B. Chen, A. H. Margaret, W. C. George, The inhibitory effect of tamoxifen on human dermal fibroblast-populated collagen lattices, Zhonghua Zheng Xing Wai Ke Za Zhi, (18(3): 160-2 (2002).

IBIS Investigators, First results from the International Breast Cancer Intervention Study (IBIS-I): a randomised prevention trial, Lancet, 360(9336): 817-24 (2002).

Jordan, V. C., Metabolites of tamoxifen in animals and man: identification, pharmacology, and significance, Breast Cancer Res. Treat., 2(2) 123-38 (1982).

Kuiper, G. G. J. M., B. Carlsson, K. Grandien, E. Enmark, J. Heggblad, S. Nilsson, J. Gustafsson, Comparison of the ligand binding specificity and transcript tissue distribution of estrogen receptors α and β, Endocrinology, 138:863-870 (1997).

Kuttenn, F. and P. Mauvais-Jarvis, Intratumoral levels and metabolism of 4-hydroxytamoxifen after percutaneous administration at the breast level, C. R. Acad. Sci. III. 300:457-462 (1985) (French).

Malet C, A. Gompel, P. Spritzer, N Bricourt, N H Yaneva, I. Mowszowicz, F. Kutten and P Mauvais Jarvis, Tamoxifen and hydroxytamoxifen isomers versus estradiol effects on normal human breast cells in culture, Cancer Research, 48: 7193-7199 (1988).

Mauvais-Jarvis, P., N. Baudot, D. Castaigne, P. Banzet, and F. Kuttenn, Z-4-hydroxytamoxifen concentration and metabolism after local percutaneous administration to human breast, Cancer Research, 46:1521-1525 (1986).

Mikulec, A. A., M. M. Hanasono, J. Lum, J. M. Kadleck, M. Kita, R. J. Koch, Effect of tamoxifen on transforming growth factor beta1 production by keloid and fetal fibroblasts, Arch. Facial Plast. Surg., 3(2): 111 (2001).

Pujol, H., J. Girault, P. Rouanet, S. Fournier, J. Grenier, J. Simony, J. B. Fourtillan, and J. L. Pujol, Phase 1 study of percutaneous 4-hydroxy-tamoxifen with analyses of 4-hydroxy-tamoxifen concentrations in breast cancer and normal breast tissue, Cancer Chemother. Pharmacol., 36:493-498 (1995).

Remington: The Science and Practice of Pharmacy, Alfonso R. Gennaro, Lippincott Williams & Wilkins, 2000, pp. 836-858.

Robertson and Katzenellenbogen, J. Org. Chem., 47: 2387 (1982).

Robertson, D. W., J. A. Katzenellenbogen, D. J. Long, E. A. Rorke and B. S. Katzenellenbogen, Tamoxifen anti estrogens. A comparison of the activity, pharmacokinetics, and metabolic activation of the E and Z isomers of tamoxifen, J. Steroid Biochemistry, 16(1):1-13 (1982).

Sauvez, F., D. Salin-Drouin, M. Attia, H. Bertheux, and R. Forster, Cutaneously applied 4-hydroxytamoxien is not carcinogenic in female rats. Carcinogenesis, 20: 843-50 (1999).

Wijayaratne, A. L., S. C. Nagel, L. A. Paige, D. J. Christensen, J. D. Norris, D. M. Fowlkes, and D. P. McDonnell, Comparative Analyses of Mechanistic Difference among Antiestrogens, Endocrinology, 140(12): 5828-5840 (1999).

What is claimed is:

1. A method of treating or reducing the risk of excessive scars, comprising locally cutaneously administering 4-hydroxy tamoxifen to a site of excessive scarring or a wound or incision at risk for developing excessive scarring.

2. A method according to claim 1, wherein said site comprises a keloid scar.

3. A method according to claim 1, wherein said site comprises a wound or incision at risk for developing a keloid scar.

4. A method according to claim 1, wherein said site comprises a hypertrophic scar.

5. A method according to claim 1, wherein said site comprises a wound or incision at risk for developing a hypertrophic scar.

6. A method according to claim 1, wherein said 4-hydroxy tamoxifen is a blend of Z and E isomers.

7. A method according to claim 1, wherein said 4-hydroxy tamoxifen is predominantly a Z isomer.

8. A method according to claim 1, wherein between about 0.25 and 3.0 µg of said 4-hydroxy tamoxifen per $cm^2$ of scar is administered per day.

9. A method according to claim 1, wherein between about 0.5 and 2.5 µg of said 4-hydroxy tamoxifen per $cm^2$ of scar is administered per day.

10. A method according to claim 1, wherein 1.0 µg of said 4-hydroxy tamoxifen per $cm^2$ of scar is administered per day.

11. A method according to claim 1, wherein 2.0 µg of said 4-hydroxy tamoxifen per $cm^2$ of scar is administered per day.

12. A method according to claim 1, wherein said 4-hydroxy tamoxifen is formulated in a percutaneous administration form selected from the group consisting of: an ointment, a cream, a patch, a gel, an emulsion, a powder, and an oil.

13. A method according to claim 1, wherein said 4-hydroxy tamoxifen is formulated in a hydroalcoholic gel.

14. A method according to claim 13, wherein said hydroalcoholic gel comprises ethyl alcohol, isopropyl myristate, and hydroxypropylcellulose.

15. A method according to claim 1, wherein said 4-hydroxy tamoxifen is formulated in a hydroalcoholic solution.

16. A method according to claim 15, wherein said hydroalcoholic solution comprises ethyl alcohol, isopropyl myristate and hydroxypropylcellulose.

17. A method according to claim 1, wherein said vehicle comprises a controlled release polymer that incorporates said 4-hydroxy tamoxifen.

18. A method according to claim 1, wherein said 4 hydroxy tamoxifen is formulated in a vehicle comprising a penetration enhancer.

19. A composition according to claim 18, wherein said penetration enhancer comprises isopropyl myristate.

* * * * *